(12) United States Patent
Jacobsen et al.

(10) Patent No.: US 7,030,109 B2
(45) Date of Patent: *Apr. 18, 2006

(54) 1,2,3,4,5,6-HEXAHYDROAZEPINO [4,5-B]INDOLES CONTAINING ARYLSULFONES AT THE 9-POSITION

(75) Inventors: Eric Jon Jacobsen, Chesterfield, MO (US); Kalpana M. Merchant, Zionsville, IN (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/423,134

(22) Filed: Apr. 25, 2003

(65) Prior Publication Data

US 2004/0054170 A1   Mar. 18, 2004

Related U.S. Application Data

(60) Continuation-in-part of application No. 10/020,549, filed on Oct. 30, 2001, now abandoned, which is a division of application No. 09/613,843, filed on Jul. 11, 2000, now Pat. No. 6,468,999.

(60) Provisional application No. 60/144,574, filed on Jul. 19, 1999.

(51) Int. Cl.
| | | |
|---|---|---|
| A61K 31/55 | (2006.01) | |
| A61K 49/04 | (2006.01) | |
| A61K 51/00 | (2006.01) | |
| C07D 487/00 | (2006.01) | |
| A61B 5/055 | (2006.01) | |

(52) U.S. Cl. ............ 514/215; 424/1.65; 424/1.81; 424/9.3; 424/9.44; 540/580

(58) Field of Classification Search ........... 514/215; 540/580
See application file for complete search history.

(56) References Cited

U.S. PATENT DOCUMENTS

| | | | |
|---|---|---|---|
| 3,576,872 A | 4/1971 | Singhal | 260/362 |
| 3,652,588 A | 3/1972 | Hester, Jr. | 260/326.3 |
| 3,676,558 A | 7/1972 | Hester, Jr. | 424/234 |
| 3,839,357 A | 10/1974 | Hester, Jr. | 260/326.5 |
| 3,914,418 A | 10/1975 | Patchett et al. | 424/230 |
| 3,948,987 A | 4/1976 | Fridinger | 260/356 F |
| 4,026,830 A | 5/1977 | Gillman et al. | 260/2 P |
| 4,239,888 A | 12/1980 | Miller | 344/309 |
| 4,298,676 A | 11/1981 | Barton et al. | 430/221 |
| 4,332,820 A | 6/1982 | Markley | 424/304 |
| 4,894,358 A | 1/1990 | Filosa et al. | 303/201 |
| 5,534,518 A | 7/1996 | Henrie, II et al. | 514/260 |
| 5,952,349 A | 9/1999 | Asberom et al. | 514/316 |

FOREIGN PATENT DOCUMENTS

| | | |
|---|---|---|
| CH | 619 460 A | 9/1980 |
| CZ | 149 525 B | 7/1973 |
| CZ | 229 033 B | 5/1984 |
| DE | 21 20 708 | 11/1972 |
| DE | 24 38 099 | 2/1976 |
| DE | 24 38 120 | 2/1976 |
| DE | 25 09 037 | 9/1976 |
| DE | 25 48 910 | 5/1977 |
| DE | 27 07 784 | 8/1977 |
| DE | 27 48 978 | 5/1979 |
| DE | 30 27 530 | 2/1982 |
| DE | 38 31 445 | 3/1990 |
| DE | 196 54 445 | 7/1998 |
| DE | 198 29 357 | 1/2000 |
| EP | 0 013 414 | 7/1980 |
| EP | 0 017 883 | 10/1980 |
| EP | 0 028 381 | 5/1981 |
| EP | 0 035 712 | 9/1981 |
| EP | 0 102 476 | 3/1984 |
| EP | 0 282 448 | 9/1988 |
| EP | 0354 303 A | 2/1990 |
| EP | 0 524 781 | 1/1993 |
| EP | 666 253 A1 | 8/1995 |
| EP | 0 930 302 | 7/1999 |
| FR | 1 489 916 | 11/1967 |
| FR | 6 699 M | 2/1969 |
| FR | 2 053 028 | 4/1971 |
| FR | 2 110 283 | 6/1972 |
| FR | 2 135 740 | 12/1972 |
| FR | 2 154 568 A | 5/1973 |

(Continued)

OTHER PUBLICATIONS (Abstract) XP-002150015—J. Med. Chem. (1969), 12, 709-11. Antimalarial compounds related to diaminodiphenyl sulfone; Henry Bader, et al.

(Continued)

*Primary Examiner*—Brenda Coleman
(74) *Attorney, Agent, or Firm*—Mehdi Ganjeizadeh; Mary Hosley; Charles W. Ashbrook

(57) ABSTRACT

The present invention discloses radioligands of 9-arylsulfone of the formula (X)

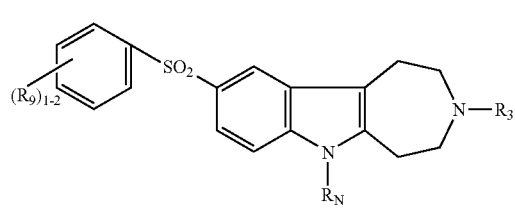

or a pharmaceutically acceptable salt or enantiomer thereof, which are useful in diagnosing depression, obesity and other CNS disorders.

17 Claims, No Drawings

FOREIGN PATENT DOCUMENTS

| | | |
|---|---|---|
| FR | 2 230 354 | 12/1974 |
| FR | 1 499 717 | 11/1996 |
| GB | 1293540 | 10/1972 |
| JP | 02 048564 | 2/1980 |
| JP | 60 044557 | 3/1985 |
| JP | 3056431 | 3/1991 |
| RU | 436 817 T | 7/1974 |
| SU | 380644 | 5/1973 |
| SU | 475382 | 6/1975 |
| WO | WO94/18980 | 9/1994 |
| WO | WO97/13748 | 4/1997 |
| WO | WO99/32463 | 7/1999 |
| WO | WO99/44618 | 9/1999 |
| WO | WO 99/62506 | 12/1999 |
| ZA | 6 801 404 1 | 8/1968 |
| ZA | 7 603 751 A | 2/1978 |

OTHER PUBLICATIONS (Abstract) XP-002150014 -Macromolecules (1988), 21 (8), 2644-7 A novel route to polypyrazoles; James A. Moore, et al.

(Abstract) XP-002150013—Khim. Geterotsikl. Soedin. (1991), (1) 54-6 Synthesis of 5-[(p-chlorophenyl) sulfonyl]indoles; N.T. Mirziashvili, et al.

(Abstract) XP-002150011—J. Chem. Eng. Data (1966), 11(4), 612-14; o-Trifluoromethylthiophenol and its derivatives; N. Sharghi, et al.

(Abstract) XP-002150010—Synthesis (1971), (7), 372-4; Aminoaryl sulfones. New preparation procedure; Everett E. Gilbert.

(Abstract) XP-002150009—J. Med. Chem. (1971), 14(12), 1166-9; Antimalarial agents. 8. Ring-substituted bis (4-aminophenyl) sulfones and their precursors; Ivan C. Popoff, et al.

(Abstract) XP-002150008—ZH. Prikl. Khim. (Leningrad) (1972), 45(12), 2704-10, Synthesis of som substituted diphenyl sulfones; I.V. Budnii, et al.

(Abstract) XP002150007—J. Mol. Struct. (1973), 16(2), 299-306, NMR data and conformational preference of o-substituted diph nyl sulfones; G. Montaudo, et al.

(Abstract) XP002150005—ZH., Khim. 1973; TR. Vses. Nauch-issled. Proekt. Inst. Monomerov (1972), 3(3), 75-80; Synthesis of 3,4,4'-triaminodipheny sulfones and their use in modifying heat-stable fibers; A. V. Ivanov, et al.

(Abstract) XP002150003—Acta Cienc. Indica (1977), 3(1), 18-19; Fries rearrangement of N-benzenesulfonylaniline; C. Srinivasan.

(Abstract) XP002150002—Khim. Geterotsikl. Soedin (1979), (7) 968-71; Synthesis and study of some bis (1', 8'-naphthoylene-1,2-benzimidazoles); A.L. Rusanov, et al.

(Abstract) XP002150001—Katalitich. Prevrashcheniya Organ. Soedin., Perm (1978) 20-5; Sulfarylation of p-substituted benzenesulfonic acid salts rin phosphoric acid; A. G. Klein, et al.

(Abstract) XP00215000—Quant. Struct.-Act. Relat. (1987), 6(4), 164-72; Multiple regression analysis of antimalarial activities of sulfones and sulfonamides in cell-free systems and principal component analysis to compare with antibacterial activities; M. Wiese, et al.

(Abstract) XP002149999—J. Med. Chem. (1989), 32(10), 2396-9; Quantitative structure-activity relationships in dihydropteroate synthase inhibition by multisubstituted sulfones. Design and synthesis of some new derivatives with improved potency; G. Pier De Benedetti, et al.

(Abstract) XP002149998—Arzneim.-Forsch. (1989), 39(9), 1081-4; Studies on 2,3,N,N'-substituted 4,4'-diaminodiphenylsulfones as potential antimalarian agents; M. Saxena, et al.

(Abstract) XP002149997—J. Clin. Invest. (1990), 85(2), 371-9; Interaction of sulfonamide and sulfone compounds with Toxoplasma gondii dihydropteroate synthase; Carmen J. Allegra, et al.

(Abstract) XP002149996—Theochem (1992), 88, 231-48; Electrostatics in quantitative structure-activity relationship analysis; P.G. De Benedetti.

(Abstract) XP002149995—J. Chem.Soc., Kerkin Trans. 1 (1992), (22), 3129-34; 2H-Benzimidazoles (isobenzimidazoles). Brian Iddon, et al.

(Abstract) XP002149994—Boll. Chim. Farm. (1994), 133(2), 72-5; Synthesis and antimicrobial evaluation of new derivatives of diphenylsulfone; A. De La Cruz, et al.

(Abstract) XP002149993—Environ. Toxicol. Pharmacol (1998) 5(2), 145-153; The effect of 2,2'-substitution on the metabolism and toxicity of dapsone in vitro and in vivo; M.D. Tingle, et al.

(Abstract) XP002149992—Bol. Soc. Chil. Quim (2000), 45(2), 181-189; Synthesis characterization and electrical properties of poly (p-phenylsulfonyl aniline); Fernando R. Diaz, et al.

(Abstract) XP002149991—Indian J. Appl. Chem. (1966), 29(2-3), 51-3; Potential fungicidal compounds. IV. Some aryl polynitrophenyl sulfones; Satya Prakash Gupta, et al.

(Abstract) XP002149990—J. Chem. Soc. C. (1968), (3), 322-7; Photochemical transformations. XXII. Reactions of 2,4-dinitrobenzenesulfenyl derivatives; Derek H. R. Barton, et al.

(Abstract) XP002149989—ZH. Fiz, Khim. (1968), 42(8), 1861-4; Interaction of functional groups through.pi.-electron systems. V. Interaction through aromatic rings connected by a monofunctional bridging group; A.E. Lutskii, et al.

(Abstract) XP002149987—Ann. Soc. Sci. Bruxelles, Ser. 1, (1969); New ph nothiazines by Smiles arrangement; R.L. Mital, et al.

(Abstract) XP002149986—J. Chem. Soc., Perkin Trans. 1 (1973), (18), 1980-3; .sigma.-Complex formulation and aromatic substitution with thiolates and nitroatyl thio ethers; Gino Biggi, et al.

(Abstract) XP-002149983—J. Org. Chem. 1975, 40(25), 3777-8; Electronic and steric effects in nucleophilic aromatic substitution. Kinetic studies on the reactions between ethers and thioethers of 2,4-dinitrophenol and nucleophiles; G. Bartoli, et al.

(Abstract) XP002149981—Chim. Acta. Turc. (1981), 9(2), 395-9; Synthesis and fungitoxicity of some substituted aryl polynitrophenyl sulfies and sulfones; Merra Katiyar, et al.

(Abstract) XP002149979—Khim. Geterotsikl. Soedin. (1968), (1), 131-6; Indole derivatives. XXIV. Synthesis of some 1,2,3,4,5,6-hexahydroazepino [4,5-b]indoles; N.M. Sharkova, et al.

(Abstract) XP002149978—Farmakol. Toksikol (Moscow), (1972), 35(3), 274-80; Pharmacological activity spectra of some azepino-and benzoxepinoindole derivatives; G. N. Artemenko, et al.

XP000650781—Journal of Medicinal Chemistry, US, American Chemical Society, Washington. vol. 11, No. 1, 1968, pp. 101-106; Azepinoindoles. I. Hexahydroazepino[4,5-b]indoles; J. B. Hester, et al.

1,2,3,4,5,6-HEXAHYDROAZEPINO [4,5-B]INDOLES CONTAINING ARYLSULFONES AT THE 9-POSITION

CROSS REFERENCE TO RELATED APPLICATIONS

This application is a continuation-in-part of U.S. application Ser. No. 10/020,549, filed 30 Oct. 2001 now abandoned, which is a divisional of U.S. application Ser. No. 09/613,843, filed 11 Jul. 2000, U.S. Pat. No. 6,468,999, which claims the benefit of U.S. provisional application Ser. No. 60/144,574, filed 19 Jul. 1999, under 35 USC 119(e)(i), which are incorporated herein by reference in their entirety.

BACKGROUND OF THE INVENTION

1. Field of the Invention

The present invention is substituted 9-arylsulfone-1,2,3,4,5,6-hexahydroazepino[4,5-b]indoles (X) having at least one radioligand which are useful for diagnosing anxiety, depression and other CNS disorders in humans and animals.

2. Description of the Related Art

U.S. Pat. No. 3,652,588 discloses 6-alkyl-1,2,3,4,5,6-hexahydroazepino[4,5-b]indoles which were useful for tranquilizing and sedating mammals to suppress hunger in mammals. This document discloses that there can be substitution at the 9-position. However, those substituents are limited to hydrogen, alkyl, alkoxy and halogen.

U.S. Pat. No. 3,839,357 discloses 6-benzyl-1,2,3,4,5,6-hexahydroazepino[4,5-b]indoles which were useful for tranquilizing mammals. This document discloses that there can be substitution at the 9-position. However, those substituents are limited to hydrogen, alkyl, alkoxy and halogen.

U.S. Pat. No. 3,676,558 discloses 6-alkyl-1,2,3,4,5,6-hexahydroazepino[4,5-b]indoles which were useful to suppress hunger in mammals. This document discloses that there can be substitution at the 9-position. However, it is limited to hydrogen, alkyl, alkoxy and halogen.

SUMMARY OF INVENTION

Disclosed are radioligands of 9-arylsulfone of the formula (X)

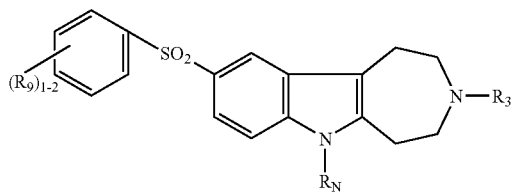

(X)

or a pharmaceutically acceptable salt or enantiomer thereof
wherein $R_3$ is:
(1) —H,
(2) $C_1$–$C_4$ alkyl,
(3) $C_0$–$C_4$ alkyl-ϕ where -ϕ is optionally substituted with up to 2 of the following:
  (a) —F, —Cl, —Br, —I,
  (b) —OH,
  (c) —$OC_1$–$C_4$ alkyl,
  (d) —$CF_3$,
  (e) —C≡N,
  (f) —$NO_2$,
where $R_N$ is:
(1) —H,
(2) $C_1$–$C_4$ alkyl,
(3) $C_0$–$C_4$ alkyl-ϕ where -ϕ is optionally substituted with up to 2 of the following:
  (a) —F, —Cl, —Br, —I,
  (b) —O—$R_{N-1}$ where $R_{N-1}$ is —H, $C_1$–$C_4$ alkyl, and -ϕ,
  (c) —$CF_3$,
  (d) —C≡N,
  (e) —$NO_2$,
where $R_9$ is:
(1) —H,
(2) —F, —Cl,
(3) $C_1$–$C_4$ alkyl,
(4) $C_1$–$C_3$ alkoxy,
(5) —$CF_3$,
(6) $C_0$–$C_4$ alkyl-ϕ where -ϕ is optionally substituted with up to 2 of the following:
  (a) —F, —Cl, —Br, —I,
  (b) —O—$R_{9-1}$ where $R_{9-1}$ is —H, $C_1$–$C_4$ alkyl, and -ϕ,
  (c) —$CF_3$,
  (d) —C≡N,
  (e) —$NO_2$
(7) —$OR_{9-1}$ where $R_{9-1}$ is as defined above, wherein the compound of formula X includes an isotopic label.

Also disclosed are the thio ethers of formula (III), the amines of formula (IV), the hydrazines of formula (V), the compounds of formula (VII), and the protected 9-arylsulfones of formula (VII) where PG is selected from the group consisting of ϕ—$CH_2$—, -ϕ—CO—, ϕ—$CH_2$—$CO_2$— and —CO—O—$C(CH_3)_3$ and where $R_9$ is as defined above.

Further disclosed is the use a 9-arylsulfone (X) and pharmaceutically acceptable salts thereof for the manufacture of a medicament for use in diagnosing a human who has a condition selected from the group consisting of anxiety, depression, schizophrenia, stress related disease, panic, a phobia, obsessive compulsive disorder, obesity, post-traumatic stress syndrome and who is in need of such treatment.

Further aspects and embodiments of the invention may become apparent to those skilled in the art from a review of the detailed description, the examples and the appended claims. The scope of the invention includes a radiolabeled compound of any one or more or combination of the examples, that are provided for exemplification and not limitation. While the invention is susceptible of embodiments in various forms, described hereafter are specific embodiments of the invention with the understanding that the present disclosure is intended as illustrative, and is not intended to limit the invention to the specific embodiments described herein. For example, the invention includes a radioligand of any one or more or combination of the following and optionally as a pharmaceutical salt:

9-(phenylsulfonyl)-1,2,3,4,5,6-hexahydroazepino[4,5-b]indole,

9-[(4-fluorophenyl)sulfonyl]-1,2,3,4,5,6-hexahydroazepino[4,5-b]indole, 6-ethyl-9-(phenylsulfonyl)-1,2,3,4,5,6-hexahydroazepino[4,5-b]indole, and 6-methyl-9-(phenylsulfonyl)-1,2,3,4,5,6-hexahydroazepino[4,5-b]indole, 3,6-dimethyl-9-(phenylsulfonyl)-1,2,3,4,5,6-hexahydroazepino[4,5-b]indole, and 3-methyl-9-(phenylsulfonyl)-1,2,3,4,5,6-hexahydroazepino[4,5-b]indole, 1-methyl-9-(phenylsulfonyl)-1,2,3,4,5,6-hexahydroazepino[4,5-b]indole, 2-methyl-9-(phenylsulfonyl)-1,2,3,4,5,6-hexahydroazepino[4,5-b]indole,
4-methyl-9-(phenylsulfonyl)-1,2,3,4,5,6-hexahydroazepino[4,5-b]indole,
5-methyl-9-(phenylsulfonyl)-1,2,3,4,5,6-hexahydroazepino[4,5-b]indole,
1,6-dimethyl-9-(phenylsulfonyl)-1,2,3,4,5,6-hexahydroazepino[4,5-b]indole,
2,6-dimethyl-9-(phenylsulfonyl)-1,2,3,4,5,6-hexahydroazepino[4,5-b]indole,
4,6-dimethyl-9-(phenylsulfonyl)-1,2,3,4,5,6-hexahydroazepino[4,5-b]indole, and
5,6-dimethyl-9-(phenylsulfonyl)-1,2,3,4,5,6-hexahydroazepino[4,5-b]indole.

DETAILED DESCRIPTION OF THE INVENTION

The unsubstituted 9-arylsulfones ($R_3$=H) and substituted 9-arylsulfones ($R_3$ is other than H) are both prepared by means known to those skilled in the art. The term 9-arylsulfones (X) includes the unsubstituted 9-arylsulfones (IX), where $R_3$ is —H. The process of preparation can be viewed as being in two parts. The first part is the production of the appropriately substituted hydrazone (V), see Scheme A.

Scheme A

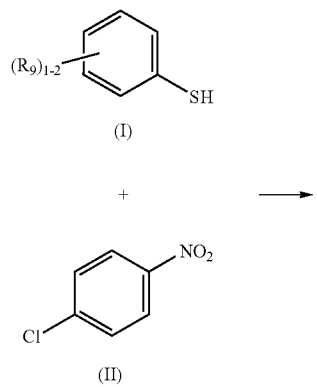

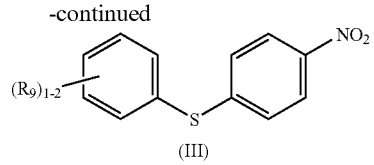

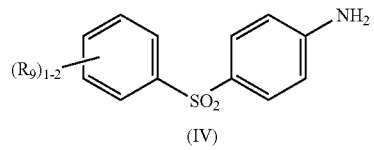

The appropriately substituted thiol (I) is coupled with the appropriately substituted 4-chloro-1-nitrobenzene (II) by known means to produce the thioether (III).

The thioether (III) is then oxidized with hydrogen peroxide (30%) followed by reduction with rhodium on carbon (5%), all of which is known to those skilled in the art, to produce the amine (IV). The amine (IV) is then diazotized by (sodium) nitrite and (hydrochloric) acid followed by reduction with tin chloride/water to give the corresponding hydrazine (V).

The appropriately substituted thiols (I) are either known to those skilled in the art or can be readily prepared from known starting materials by means well known to those skilled in the art. It is preferred that the $R_9$ substituent be in either the 3- or 4-position.

The second part is the coupling and reaction of the appropriately substituted hydrazone (V) with the 1-protected hexahydro-4H-azepine-4-one (VI) to give the intermediate (VII) and its transformation to the unsubstituted 9-arylsulfone (IX), see Scheme B.

Scheme B

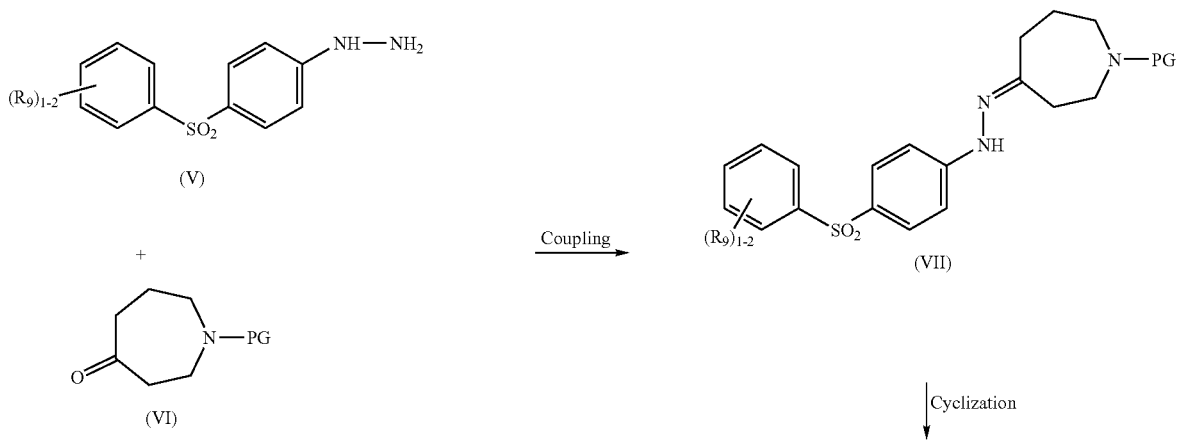

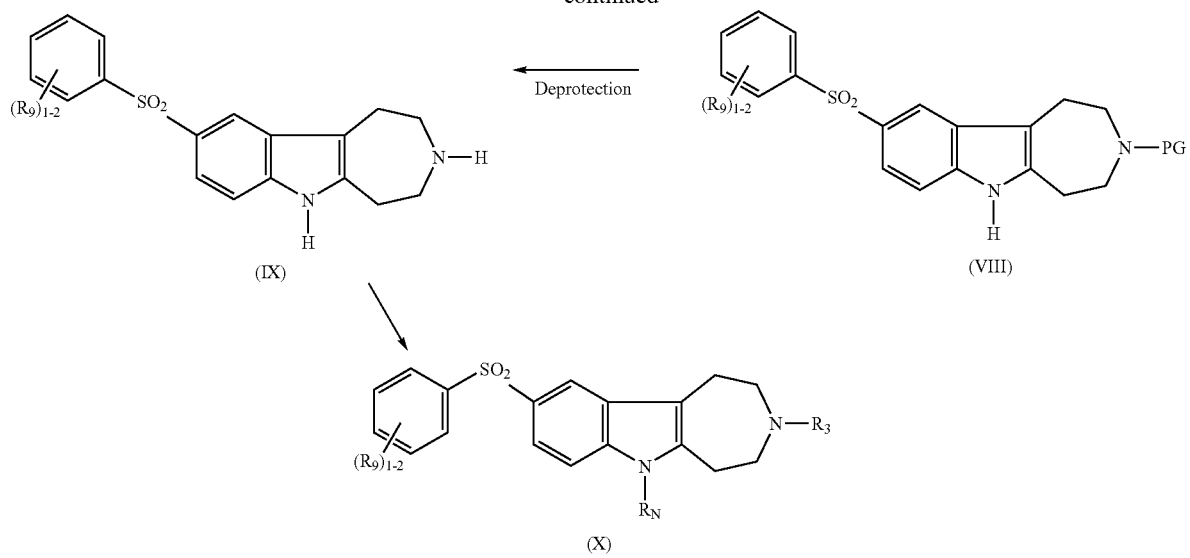

The second part of the reaction is well known to those skilled in the art, see U.S. Pat. Nos. 3,652,588, 3,676,558 and 3,839,357. The only difference between the process in those patents and that here is the arylsulfone substituent at the 9-position. That substituent is already in place in the hydrazine (V) prior to the reaction of the 9-arylsulfone hydrazine (V) with the 1-protected hexahydro-4H-azepine-4-one (VI) to produce the correspondingly substituted intermediate (VII). Suitable protecting groups (PG) include φ—CH$_2$—, φ—CO—, φ—CH$_2$—CO$_2$— and —CO—O—C(CH$_3$)$_3$; it is preferred that the protecting group be φ—CH$_2$— or φ—CO—. The cyclization of the intermediate (VII) to the corresponding protected arylsulfone (VIII) and then the deprotection to the unsubstituted 9-arylsulfone (IX) all follow known methods. The protecting groups (PG) are readily removed by means well known to those skilled in the art. The unsubstituted 9-arylsulfone (IX) can then be substituted at the C3-position (R$_3$, ring nitrogen atom) as well as on the indole nitrogen (R$_N$) as is known to those skilled in the art. Alternatively, arylsulfone (VIII) can be alkylated with the desired R$_N$-X substituent to give the protected indole (XI) which then is deprotected to give the desired substituted 9-arylsulfone (X). Useful R$_3$ groups include —H and C$_1$–C$_2$ alkyl; it is preferred that R$_3$ be —H. Useful R$_N$ groups include —H and C$_1$–C$_4$ alkyl; it is preferred that R$_N$ is —H, C$_1$ alkyl and C$_2$ alkyl. The invention here is not the process chemistry but rather the novel products produced.

The preferred protecting group for the intermediates (VI), (VII) and (VIII) are benzyl and benzamide though other groups are operable as is known to those skilled in the art.

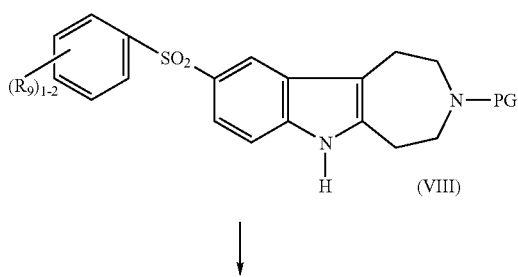

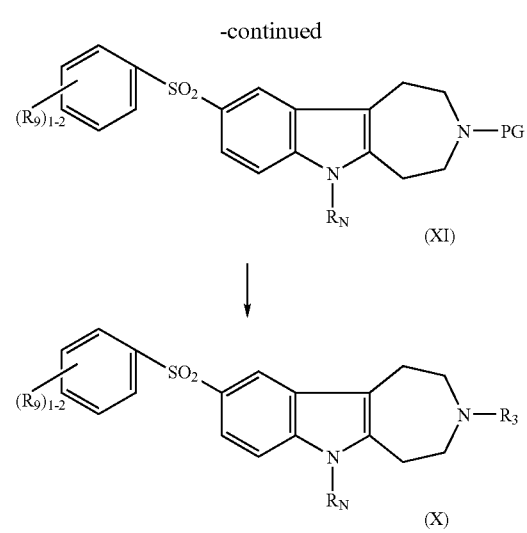

The 9-arylsulfones (XI) are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids methanesulfonic, hydrochloric, hydrobromic, sulfuric, phosphoric, nitric, benzoic, citric, tartaric, fumaric, maleic, CH$_3$—(CH$_2$)$_n$—COOH where n is 0–4, HOOC—(CH$_2$)$_n$—COOH where n is 0–4.

The invention also provides a method of utilizing an isotopically labeled compound of formula X to perform diagnostic screening, such as positron emission tomography, single photon emission computed tomography, and nuclear magnetic resonance spectroscopy.

The compounds of the present invention are useful in diagnostic analysis of a diseases or conditions of the central nervous system in a mammal. The present invention further provides compounds that are useful in diagnostic analysis of a disease or condition in a mammal, such as where a 5-HT receptor is implicated and modulation of a 5-HT function is desired or where a 5-HT$_6$ receptor is implicated and modulation of a 5-HT$_6$ function is desired. The 9-arylsulfones (X) of the present invention are useful to diagnose CNS disorders, including, but not limited to, any one of the following: anxiety, depression, schizophrenia, stress related disease, panic, a phobia, obsessive compulsive disorder, obeisity, or post-traumatic stress syndrome. It is preferred that the 9-aryl sulfones (X) be used to diagnose anxiety or depression.

The isotopically-labeled compounds may be prepared following conventional methods in analogy to the synthesis of the 9-arylsulfones (X) described herein. As shown below, treatment of 9-arylsulfones (X) with $^{11}CH_3I$ in the presence of a suitable base (for example, but not limitation, pyridine or triethylamine) after purification by HPLC provides an arylsulfone with a radiolabel.

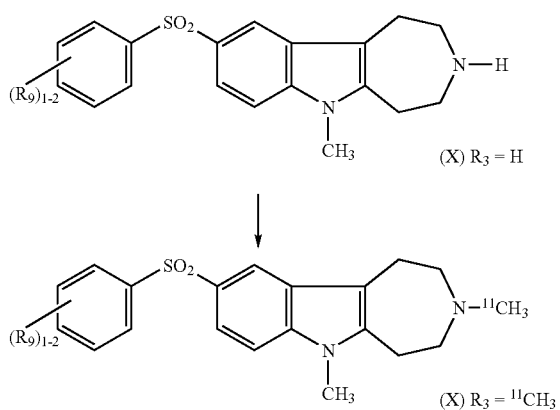

Alternatively, treatment of VIII with sodium hydride and $^{11}CH_3I$ in THF provides XI, which after deprotection and HPLC purification, provides an arylsulfone with a radiolabel. The PG group may also be alkyl, eliminating the deprotection step.

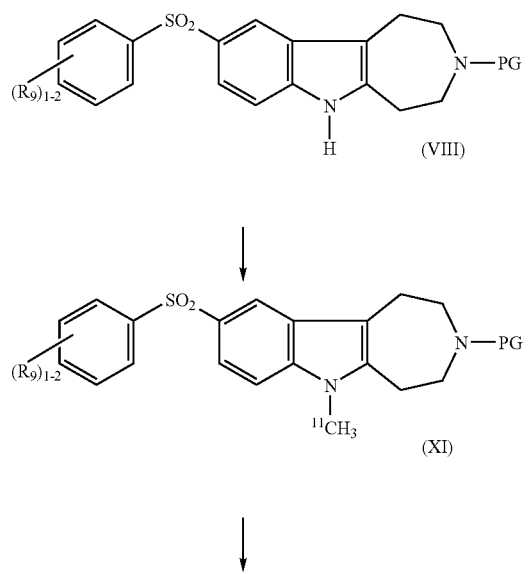

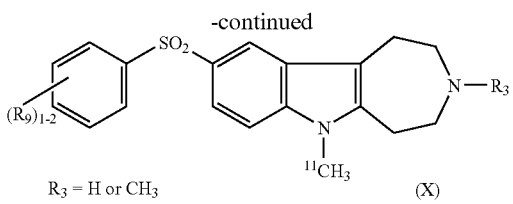

Compounds of the present invention may be administered in a pharmaceutical composition containing the compound in combination with a suitable vehicle. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention are administered parenterally (for example, by intravenous, intraperitoneal or intramuscular injection). The compounds or compositions may be administered by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. In many cases, it will be preferable to include isotonic agents, for example, sugars, buffers or sodium chloride.

Sterile injectable solutions can be prepared by incorporating the active compound in the required amount in the appropriate solvent with various of the other ingredients enumerated above, as required, followed by filter sterilization.

Useful liquid carriers include water, alcohols or glycols or water-alcohol/glycol blends, in which the present compounds can be dissolved or dispersed at effective levels, optionally with the aid of non-toxic surfactants.

Generally, compounds of the invention are 5-HT ligands. The ability of a compound of the invention to bind or act at a 5-HT receptor, or to bind or act selectively at a specific 5-HT receptor subtype can be determined using in vitro and in vivo assays that are known in the art. As used herein, the term "bind selectively" means a compound binds at least 2 times, preferably at least 10 times, and more preferably at least 50 times more readily to a given 5-HT subtype than to one or more other subtypes. Preferred compounds of the invention bind selectively to one or more 5-HT receptor subtypes.

The ability of a compound of the invention to act as a 5-HT receptor agonist or antagonist can also be determined using in vitro and in vivo assays that are known in the art. The invention provides isotopically labeled compounds of formula X that act as either agonists or as antagonists of one or more 5-HT receptor subtypes.

In general, radiolabeled compounds of formula X that are useful in performing PET or SPECT are those which penetrate the blood-brain barrier, exhibit high selectivity, high affinity to 5-HT$_6$ serotonin receptors, and are eventually metabolized. Compounds that are non-selective or those that exhibit excessive or limited affinity for 5-HT$_6$ serotonin receptors are, generally, not useful in studying brain receptor binding kinetics with respect to 5-HT$_6$ serotonin receptors. Compounds that are not metabolized may pose safety risks. A mammal is injected with a radioactively labeled agent at tracer doses. Tracer doses are doses sufficient to allow the receptor occupancy to be measured (e.g., to allow detection of the labeled compound) but are not sufficient to have a therapeutic effect on the mammal. Tracer dosage is generally between approximately $\frac{1}{100}$ to approximately $\frac{1}{10}$ of the therapeutic dose. The radiolabeled compound of formula X is generally administered once daily and is generally administered intravenously. Methods for the extrapolation of effective dosages in mice, and other animals, to humans are known to the art; for example, see U.S. Pat. No. 4,938,949. The therapeutic dosage range for the compound of the present invention is from about 0.0001 to about 1 mg/day, or any range therein, of active ingredient per unit dosage form (e.g., per kg of mammal body weight). The compound of formula X (radiolabeled) is generally administered once daily and is generally administered intravenously.

The exact dosage and frequency of administration depends on the particular 9-arylsulfone(s) used, the particular disease being diagnosed, the severity of the disease being diagnosed, the age, weight, general physical condition of the particular patient, other medication the individual may be taking as is well known to those skilled in the art and can be more accurately determined by measuring the blood level or concentration of the 9-arylsulfone (X) in the patient's blood.

DEFINITIONS AND CONVENTIONS

The definitions and explanations below are for the terms as used throughout this entire document including both the specification and the claims.

I. Conventions For Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta ($\beta$) configuration and is indicated by an unbroken or solid line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents a-$R_{i-j}$ and $\beta$-$R_{i-k}$. When a bivalent variable, $R_i$, is defined to consist of two monovalent variable substituents, the convention used to define the bivalent variable is of the form "a-$R_{i-j}$:$\beta$-$R_{i-k}$" or some variant thereof. In such a case both a-$R_{i-j}$ and $\beta$3-$R_{i-k}$ are attached to the carbon atom to give —C(a-$R_{i-j}$)($\beta$-$R_{i-k}$)—. For example, when the bivalent variable $R_6$, —C(=$R_6$)— is defined to consist of two monovalent variable substituents, the two monovalent variable substituents are a-$R_{6-1}$:$\beta$-$R_{6-2}$, . . . a-$R_{6-9}$:$\beta$-$R_{6-10}$, etc., giving —C(a-$R_{6-1}$)($\beta$-$R_{6-2}$)—, . . . —C(a-$R_{6-9}$)($\beta$-$R_{6-10}$)—, etc. Likewise, for the bivalent variable $R_{11}$, —C(=$R_{11}$)—, two monovalent variable substituents are a-$R_{11-1}$:$\beta$-$R_{11-2}$. For a ring substituent for which separate a and $\beta$ orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —C$_1$(R$_i$)H—C$_2$(R$_j$)H— (C$_1$ and C$_2$ define arbitrarily a first and second carbon atom, respectively) R$_i$ and R$_j$ may be defined to be taken together to form (1) a second bond between C$_1$ and C$_2$ or (2) a bivalent group such as oxa (—O—) and the formula thereby describes an epoxide. When R$_i$ and R$_j$ are taken together to form a more complex entity, such as the group —X—Y—, then the orientation of the entity is such that C$_1$ in the above formula is bonded to X and C$_2$ is bonded to Y. Thus, by convention the designation " . . . R$_i$ and R$_j$ are taken together to form —CH$_2$—CH$_2$—O—CO— . . . " means a lactone in which the carbonyl is bonded to C$_2$. However, when designated " . . . R$_j$ and R$_i$ are taken together to form —CO—O—CH$_2$—CH$_2$—" the convention means a lactone in which the carbonyl is bonded to C$_1$.

The carbon atom content of variable substituents is indicated in one of two ways. The first method uses a prefix to the entire name of the variable such as "C$_1$–C$_4$", where both "1" and "4" are integers representing the minimum and maximum number of carbon atoms in the variable. The prefix is separated from the variable by a space. For example, "C$_1$–C$_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus, C$_2$–C$_4$ alkoxycarbonyl describes a group CH$_3$—(CH$_2$)$_n$—O—CO— where n is zero, one or two. By the second method the carbon atom content of only each portion of the definition is indicated separately by enclosing the "C$_i$–C$_j$" designation in parentheses and placing it immediately (no intervening space) before the portion of the definition being defined. By this optional convention (C$_1$–C$_3$)alkoxycarbonyl has the same meaning as C$_2$–C$_4$ alkoxy-carbonyl because the "C$_1$–C$_3$" refers only to the carbon atom content of the alkoxy group. Similarly while both C$_2$–C$_6$ alkoxyalkyl and (C$_1$–C$_3$)alkoxy(C$_1$–C$_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the Schemes which will also set forth the chemical structural formula of that particular substituent.

II. DEFINITIONS

All temperatures are in degrees Centigrade.

HPLC refers to high pressure liquid chromatography.

DMSO refers to dimethylsulfoxide.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

IR refers to infrared spectroscopy.

NMR refers to nuclear (proton) magnetic resonance spectroscopy, chemical shifts are reported in ppm (d) downfield from tetramethylsilane.

-ϕ refers to phenyl (C$_6$H$_5$).

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

The invention also includes isotopically-labeled compounds, which are identical to those recited in Formula X, where one or more atoms is replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{13}$N, $^{15}$O, $^{18}$F, $^{99m}$Tc, $^{123}$I, and $^{125}$I. Compounds of the present invention and pharmaceutically acceptable salts and prodrugs of said compounds that contain the aforementioned isotopes and/or other isotopes of other atoms are within the scope of the invention. Isotopically-labeled compounds can be prepared as follows. Carbon, nitrogen, oxygen, and fluorine atoms in a molecule may be replaced by isotopic versions of carbon, nitrogen, oxygen, and fluorine, respectively. Of particular usefulness are reagents containing isotopic carbon.

Isotopically-labeled compounds of the present invention are useful in drug and/or substrate tissue distribution and target occupancy assays. For example, isotopically labeled compounds are particularly useful in SPECT (single photon emission computed tomography) and in PET (positron emission tomography).

Single-photon emission computed tomography (SPECT), acquires information on the concentration of isotopically labeled compounds introduced to a mammal's body. SPECT dates from the early 1960's, when the idea of emission traverse section tomography was introduced by D. E. Kuhl and R. Q. Edwards prior to either PET, x-ray CT, or MRI. In general, SPECT requires isotopes that decay by electron capture and/or gamma emission. Example of viable SPECT isotopes include, but are not limited to, 123-iodine ($^{123}$I) and 99m-technetium ($^{99m}$Tc).

The nuclear decay resulting in the emission of a single gamma ray which passes through the tissue and is measured externally with a SPECT camera. The uptake of radioactivity reconstructed by computers as a tomogram shows tissue distribution in cross-sectional images.

Positron emission tomography (PET) is a technique for measuring the concentrations of positron-emitting isotopes within the tissues. Like SPECT, these measurements are, typically, made using PET cameras outside of the living subjects. PET can be broken down into several steps including, but not limited to, synthesizing a compound to include a positron-emitting isotope; administering the isotopically labeled compound to a mammal; and imaging the distribution of the positron activity as a function of time by emission tomography. PET is described, for example, by Alavi et al. in Positron Emission Tomography. published by Alan R. Liss, Inc. in 1985.

Positron-emitting isotopes used in PET include, but are not limited to, Carbon-11, Nitrogen-13, Oxygen-15, and Fluorine-18. In general, positron-emitting isotopes should have short half-lives to help minimize the long term radiation exposure that a patient receives from high dosages required during PET imaging.

In certain instances, PET imaging can be used to measure the binding kinetics of compounds of this invention with 5-HT$_6$ serotonin receptors. For example, administering an isotopically labeled compound of the invention that penetrates into the body and binds to a 5-HT$_6$ serotonin receptor creates a baseline PET signal which can be monitored while administering a second, different, non-isotopically labeled compound. The baseline PET signal will decrease as the non-isotopically labeled compound competes for the binding to the 5-HT$_6$ serotonin receptor.

In general, compounds of formula X that are useful in performing PET or SPECT are those which penetrate the blood-brain barrier, exhibit high selectivity and modest affinity to 5-HT$_6$ serotonin receptors, and are eventually metabolized. Compounds that are non-selective, exhibit excessive or small affinity for 5-HT$_6$ serotonin receptors, or exhibit low penetration through the blood-brain barrier are, generally, not useful in studying brain receptor binding kinetics with respect to 5-HT$_6$ serotonin receptors. Compounds that are not metabolized may harm the patient. Methods for determining the blood-brain penetration and the affinity for 5-HT$_6$ serotonin receptors are described below.

In other embodiments, nuclear magnetic resonance spectroscopy (MRS) imaging can be used to detect the overall concentration of a compound or fragment thereof containing nuclei with a specific spin. In general, the isotopes useful in MRS imaging include, but are not limited to, hydrogen-1, carbon-13, phosphorus-31, and fluorine-19.

Further, substitution with heavier isotopes such as deuterium, i.e., $^2$H, can afford certain therapeutic advantages resulting from greater metabolic stability, for example increased in vivo half-life or reduced dosage requirements and, hence, maybe preferred in some circumstances.

Pharmaceutically acceptable salts may be obtained using standard procedures well known in the art, for example by mixing a compound of the present invention with a suitable acid.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

1-[4-(Phenylsulfonyl)phenyl]hydrazine (V)

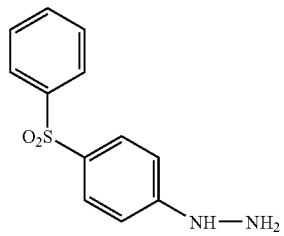

A mixture of 4-chlorophenyl phenyl sulfone (10.1 g, 40.0 mmol), hydrazine monohydrate (30 mL), and triethylamine (4 drops) in ethylene glycol (20 mL) is heated at 150° for 15 hr. Upon cooling, the mixture is diluted with H$_2$O and filtered. The residual solid is washed with H$_2$O until the washings are neural (pH=6). This material is then triturated with methylene chloride and dried under reduced pressure at 50° to give the title compound, IR (drift) 3282, 1586, 1514, 1306, 1291, 1158, 1145, 1104, 996, 813, 756, 730, 717, 688 and 678 cm$^{-1}$; NMR (300 MHz, CDCl$_3$) 7.70–7.85, 7.45–7.65, 6.79 and 4.22 δ; MS (EI) m/z 248 (M$^+$), 125, 123, 108, 107, 90, 80, 77, 63 and 51.

PREPARATION 2

1-[4-[(4-Fluorophenyl)sulfonyl]phenyl]hydrazine (V)

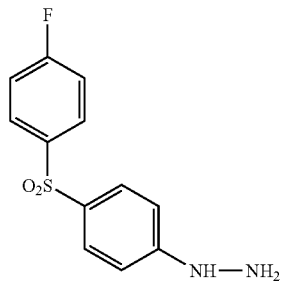

Step I: 4-Fluorophenyl-4-nitrophenyl Sulfide (III)

A mixture of 4-fluorothiophenol (I, 2.08 g, 19.5 mmol), 1-chloro-4-nitrobenzene (II, 3.39 g, 21.5 mmol), and potassium carbonate (5.40 g, 39.0 mmol) in acetonitrile (75 mL) is stirred at 20–25° under nitrogen for 16 hr. The mixture is diluted with H$_2$O (100 mL) and extracted into methylene chloride (3×100 mL). The extracts are dried over anhydrous magnesium sulfate, filtered, and concentrated under reduced pressure to provide a quantitative yield of the desired thioether, mp=84–90°; NMR (300 MHz, CDCl$_3$) 8.07, 7.45–7.60 and, 7.05–7.25 δ.

Step II: 4-[(4-Fluorophenyl)sulfonyl]phenylamine (IV)

A hot mixture (100°) of 4-fluorophenyl 4-nitrophenyl sulfide (III, Step I, 1.91 g, 7.66 mmol) in glacial acetic acid (50 mL) is treated with hydrogen peroxide (30%, 2.60 mL), followed 20 min later by a second portion of hydrogen peroxide (30%, 1.70 mL). The mixture continued to heat for an additional 30 min, and is then allowed to cool to 20–25°. The mixture is concentrated to near dryness and filtered, rinsing the solid with H₂O. The solid is dried in a vacuum oven at 50° to give the intermediate sulfone, IR (drift) 1590, 1534, 1356, 1307, 1294, 1242, 1166, 1156, 1109, 1101, 858, 839, 742, 687 and 665 cm⁻¹; NMR (300 MHz, CDCl₃) 8.35, 8.12, 7.95–8.05 and 7.15–7.30 δ; MS (EI) m/z 281 (M⁺), 159, 143, 111, 95, 95, 83, 76, 74 and 51.

A mixture of 4-fluorophenyl 4-nitrophenyl sulfone (1.89 g, 6.72 mmol) in methanol (80 mL) is treated with Rhodium on carbon (5%, 95 mg) and hydrogenated at 20 psi for 24 hr. The mixture is filtered, rinsing with methylene chloride (2×100 mL) and methanol (100 mL). The filtrate is concentrated to near dryness and refiltered, rinsing with minimal methanol. The solid is dried in the vacuum oven at 500 to give the desired amine, mp=204–205°: IR (drift) 3473, 3373, 1638, 1592, 1489, 1303, 1294, 1285, 1231, 1159, 1144, 1107, 834, 713 and 689 cm⁻¹; NMR (300 MHz, CDCl3) 7.80–7.95, 7.60–7.75, 7.13, 6.60–6.75 and 4.17 δ; MS (EI) m/z 251 (M⁺), 140, 108, 95, 92, 80, 65, 65, 63 and 51.

Step III: 1-[4-[(4-Fluorophenyl)sulfonyl]phenyl]hydrazine (V)

A mixture of 4-[(4-fluorophenyl)sulfonyl]phenylamine (IV, Step II, 3.10 g, 12.3 mmol) in concentrated hydrochloric acid (30 mL) at 0° is treated with sodium nitrite (934 mg, 13.5 mmol) in H₂O (15 mL). After 30 min, the mixture is treated with stannous chloride (5.57 g, 24.7 mmol) in concentrated hydrochloric acid (15 mL). The mixture is stirred at 0° for 1 hr, and then at 20–25° for 1 hr. The precipitate is collected and slurried in H₂O. The mixture is made basic (sodium hydroxide, 50%) and the solid isolated. The material is partitioned between methylene chloride and saline. The organic layer is dried, filtered, and concentrated under reduced pressure to give the title compound, NMR (300 MHz, CDCl₃) 7.85–7.95, 7.74, 7.13, 6.85, 5.64 and 3.65 δ.

Example 1

9-(Phenylsulfonyl)-1,2,3,4,5,6-hexahydroazepino[4,5-b]indole (IX)

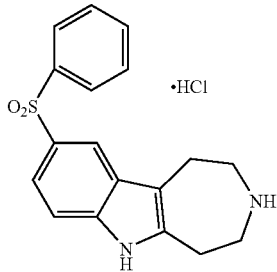

Step I: 1-Benzyl-4-azepanone N-[4-(Phenylsulfonyl)phenyl]hydrazone (VII)

A mixture of 1-[4-(phenylsulfonyl)phenyl]hydrazine (V, PREPARATION 1, 7.06 g, 28.4 mmol) and 4-benzylazapanone (VI, 5.78 g, 28.4 mmol) in ethanol (130 mL) is treated with glacial acetic acid (8 drops) and heated at reflux for 1 hr. Upon cooling, the precipitate is collected, washed with ethanol and dried in the vacuum oven at 50° to give the desired compound, mp=142–146°. The filtrate is concentrated and purified via flash chromatography (ethyl acetate/heptane; 65/35) to provide additional product as two regioisomers. Analytical data for one isomer: IR (drift) 1593, 1511, 1323, 1301, 1261, 1148, 1106, 833, 758, 748, 735, 709, 689 and 600 cm⁻¹; NMR (300 MHz, CDCl₃) 7.85–7.95, 7.77, 7.40–7.65, 7.15–7.35, 7.06, 3.65, 2.65–2.85, 2.55–2.65, 2.35–2.45 and, 1.70–1.85; MS (EI) m/z 433 (M⁺), 186, 120, 108, 97, 96, 91, 82, 77, 65 and 51. Analytical data for the slower eluting isomer: IR (drift) 1593, 1509, 1324, 1296, 1285, 1264, 1148, 1106, 1085, 1069, 834, 735, 710, 688 and 605 cm⁻¹; NMR (300 MHz, CDCl₃) 7.85–7.95, 7.70–7.85, 7.35–7.55, 7.15–7.35, 7.06, 3.60, 2.55–2.75, 3.32–2.45 and 1.85–2.00; MS (EI) m/z 433 (M⁺), 187, 186, 120, 108, 97, 91, 82, 77, 65 and 51.

Step II: 3-Benzyl-9-(phenylsulfonyl)-1,2,3,4,5,6-hexahydroazepino[4,5-b]indole (VIII)

A mixture of 1-benzyl-4-azepanone N-[4-(phenylsulfonyl)phenyl]hydrazone (VII, Step I, 3.41 g, 7.86 mmol) and polyphosporic acid (4.78 g) in o-xylene (550 mL) is heated at 100° under nitrogen for 3 hr. Upon cooling, the xylene is decanted and the residual material partitioned between methylene chloride/methanol and sodium hydroxide (0.5 M). The phases are separated and the aqueous layer is further extracted with more methylene chloride/methanol (2×). The organic phases are combined and dried over anhydrous magnesium sulfate, filtered, and concentrated under reduced pressure to give an oil. The oil is purified by flash chromatography (Biotage 40M; ethyl acetate/heptane, 7/3) to give the desired indole, mp=86–88°, dec; IR (drift) 3343, 2910, 1475, 1449, 1337, 1301, 1146, 1131, 1090,748, 731, 719, 698, 688 and 627 cm⁻¹; NMR (300 MHz, CDCl₃) 8.10–8.20, 8.06, 7.96, 7.66, 7.25–7.55, 3.85 and 2.90–3.05 δ; MS (EI) m/z 416 (M⁺), 296, 154, 146, 134, 134, 132, 120, 91 and 65.

Step III: 9-(Phenylsulfonyl)-1,2,3,4,5,6-hexahydroazepino[4,5-b]indole (IX)

A mixture of 3-benzyl-9-(phenylsulfonyl)-1,2,3,4,5,6-hexahydroazepino[4,5-b]indole (VIII, Step II, 453 mg, 1.09 mmol) in methanol (50 mL) is treated with palladium hydroxide (118 mg) and hydrogenated at 30 psi for 5 days. The mixture is filtered, rinsing with methanol and methylene chloride, and the filtrate concentrated under reduced pressure to give an amorphous solid. The material is purified by flash chromatography (Biotage 40M; methanol/methylene chloride, 5/95; methanol/methylene chloride/ammonium hydroxide, 20/79/1) to give the title compound. Analytical data for the hydrochloride salt, mp=290–291.5°; IR (drift) 3382, 2751, 2698, 2689, 2646, 2438, 1297, 1150, 1131, 1095, 801, 759, 722, 684 and 616 cm⁻¹; NMR (300 MHz, DMSO-d₆) 11.65, 7.35, 8.05–8.15, 7.85–7.95, 7.40–7.65, 3.20–3.40 and 3.10–3.25 δ; MS (EI) m/z 326 (M⁺), 298, 297, 286, 285, 284, 143 and 77; HRMS (FAB) calculated for C₁₈H₁₉N₂O₂S=327.1167, found 327.1165.

Example 2

9-[(4-Fluorophenyl)sulfonyl]-1,2,3,4,5,6-hexahydroazepino[4,5-b]indole (IX)

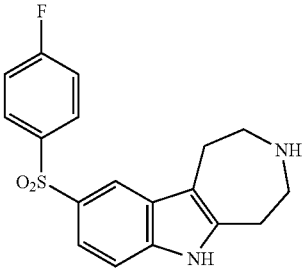

Following the general procedure of EXAMPLE 1 (Steps I-III) and making non-critical variations, 1-[4-[(4-fluorophenyl)sulfonyl]phenyl]hydrazine (V, PREPARATION 2) is converted to the title compound, mp=168°, dec.; IR (drift) 2923, 1590, 1491, 1475, 1336, 1308, 1287, 1236, 1147, 1131, 1089, 837, 816, 749 and 683 cm$^{-1}$; NMR (300 MHz, CDCl$_3$) 8.05–8.15, 8.05, 7.90–8.00, 7.55–7.65, 7.30–7.35, 7.12, 3.05–3.15 and 2.90–3.00 δ; HRMS (FAB) calculated for C$_{18}$H$_{18}$FN$_2$O$_2$S=345.1073, found 345.1087.

Example 3

9-[(4-Methylphenyl)sulfonyl]-1,2,3,4,5,6-hexahydroazepino[4,5-b]indole (IX)

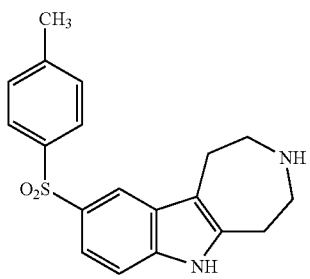

Following the general procedure of EXAMPLE 1 (Steps I–III) and making non-critical variations, 1-[4-[(4-methylphenyl)sulfonyl]phenyl]hydrazine (V, PREPARATION 2) is converted to the title compound, mp=125°, dec; IR (drift) 3027, 2921, 2830, 1475, 1453, 1336, 1298, 1287, 1150, 1130, 1090, 812, 747, 682 and 658 cm$^-$; NMR (300 MHz, CDCl$_3$) 8.12, 7.83, 7.55–7.65, 7.20–7.35, 3.05–3.20, 2.90–3.05 and 2.36 δ; MS (EI) m/z 340 (M$^+$), 311, 298, 154, 144, 143, 115, 91, 91 and 65; HRMS (FAB) calculated for C$_{19}$H$_{21}$N$_2$O$_2$S=341.1324, found 341.1311.

Example 4

9-[(4-Methoxyphenyl)sulfonyl]-1,2,3,4,5,6-hexahydroazepino[4,5-b]indole (IX)

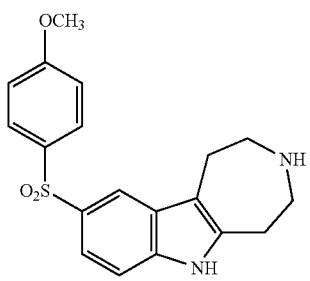

Following the general procedure of EXAMPLE 1, and making non-critical variations, 1-[4-[(4-methylphenyl)sulfonyl]phenyl]hydrazine (V, PREPARATION 2) is converted to the title compound, mp=139°, dec.; IR (drift) 2927, 2837, 1593, 1496, 1335, 1312, 1293, 1260, 1142, 1130, 1092, 834, 802, 748 and 683 cm$^{-1}$; NMR (300 MHz, DMSO-d$_6$) 11.30, 7.90–8.00, 7.75–7.85, 7.40–7.50, 7.30–7.40, 7.00–7.10, 3.77 and 2.75–3.05; MS (EI) m/z 356 (M$^+$), 327, 314, 155, 154, 143, 143, 115, 77 and 57; HRMS (FAB) calculated for C$_{19}$H$_{21}$N$_2$O$_3$S=357.1273, found 357.1275.

Example 5

9-[(3-Fluorophenyl)sulfonyl]-1,2,3,4,5,6-hexahydroazepino[4,5-b]indole (IX)

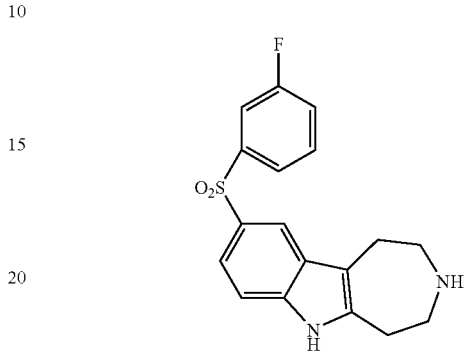

Following the general procedure of EXAMPLE 1, and making non-critical variations, 1-[4-[(3-fluorophenyl)sulfonyl]phenyl]hydrazine (V, PREPARATION 2) is converted to the title compound, mp=153–156°: IR (drift) 2926, 2867, 2855, 1474, 1311, 1296, 1225, 1151, 1129, 1082, 773, 742, 698, 677 and 629 cm$^{-1}$; NMR (300 MHz, DMSO-d$_6$) 11.37, 8.00–8.10, 7.70–7.80, 7.30–7.75 and 2.75–2.95 δ; MS (EI) m/z 344 (M$^+$), 315, 302, 154, 144, 143, 128, 128, 115 and 73; HRMS (FAB) calculated for C$_{18}$H$_{18}$FN$_2$O$_2$S=345.1073, found 345.1075.

Example 6

9-[(3-Methoxyphenyl)sulfonyl]-1,2,3,4,5,6-hexahydroazepino[4,5-b]indole hydrochloride (IX)

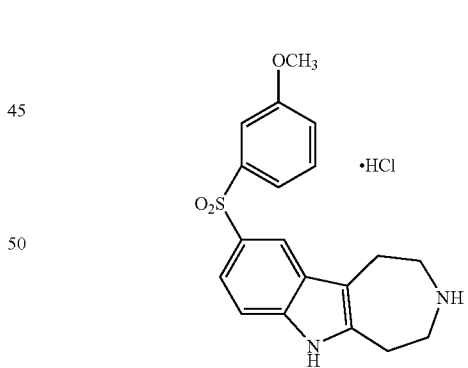

Following the general procedure of EXAMPLE 1, and making non-critical variations, 1-[4-[(3-methoxyphenyl)sulfonyl]phenyl]hydrazine (V, PREPARATION 2) is converted to the title compound, mp=232–235°, dec.; IR (drift) 2976, 2963, 2832, 2805, 2770, 2739, 1475, 1303, 1248, 1151, 1141, 746, 694, 682 and 629 cm$^{-1}$; NMR (300 MHz, DMSO-d$_6$) 11.63, 9.31, 8.10–8.15, 7.35–7.60, 7.10–7.20, 3.79, 3.20–3.40 and 3.05–3.40 δ; MS (EI) m/z 356 (M$^+$), 327, 314, 107, 74, 73, 59, 57, 57 and 56; MS (FAB) m/z 357 (MH$^+$), 356, 328, 177, 155, 121, 103, 89; HRMS (FAB) calculated for C$_{19}$H$_{21}$N$_2$O$_3$S=357.1273, found 357.1277.

Example 7

9-[(4-Trifluoromethyphenyl)sulfonyl]-1,2,3,4,5,6-hexahydroazepino[4,5-b]indole hydrochloride (IX)

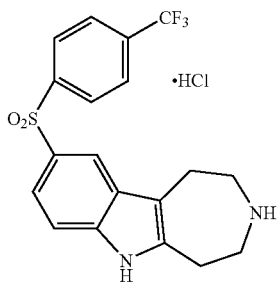

Following the general procedure of EXAMPLE 1, and making non-critical variations, 1-[4-[(4-trifluoromethylphenyl)sulfonyl]phenyl]hydrazine (V, PREPARATION 2) is converted to the title compound, mp=278–279°, dec.; IR (drift) 2773, 2756, 2732, 1321, 1306, 1178, 1156, 1133, 1122, 1108, 1061, 844, 716, 623 and 618 cm$^{-1}$; NMR (300 MHz, DMSO-d$_6$) 8.05–8.20, 7.90–8.00, 7.55–7.45, 7.45–7.55 and 3.05–3.40 δ; MS (EI) m/z 394 (M$^+$), 365, 352, 154, 143, 73, 71, 59, 58 and 57.

Example 8

6-Ethyl-9-(phenylsulfonyl)-1,2,3,4,5,6-hexahydroazepino[4,5-b]indole (IX)

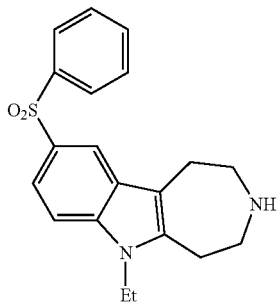

Step I: 3-Benzyl-6-ethyl-9-(phenylsulfonyl)-1,2,3,4,5,6-hexahydroazepino[4,5-b]indole A 0° mixture of 3-benzyl-9-(phenylsulfonyl)-1,2,3,4,5,6-hexahydroazepino[4,5-b]indole (EXAMPLE 1, Step II, 301 mg, 0.723 mmol) in dry DMF (5 mL) is treated with sodium hydride (60% in oil, 32 mg, 0.795 mmol), and allowed to warm to 20–25° over 1.5 hr. The mixture is then cooled (0°), treated with iodoethane (64 μL, 0.795 mmol) and allowed to slowly warm to 20–25° under nitrogen over 72 hr. The resultant mixture is diluted with ethyl acetate (50 mL) and washed with H$_2$O (3×25 mL) and saline (25 mL). The organic layer is dried over anhydrous magnesium sulfate, filtered, and concentrated under reduced pressure to give a solid. The solid is purified via chromatography (20 g SG; ethyl acetate/heptane, 65/35) to give the indole as a solid, mp=188–191°; IR (drift) 1477, 1373, 1300, 1289, 1157, 1148, 1094, 766,756, 738,728, 701, 694, 645 and 621 cm$^{-1}$; NMR (300 MHz, CDCl$_3$) 8.10–8.20, 7.90–8.05, 7.65–7.75, 7.20–7.50, 4.11, 3.82, 2.85–3.05 and 1.27 δ; MS (EI) m/z 444 (M$^+$), 326, 324, 312, 167, 154, 132, 118, 96, 91 and 64.

Step II: 6-Ethyl-9-(phenylsulfonyl)-1,2,3,4,5,6-hexahydroazepino[4,5-b]indole (X)

A mixture of 3-benzyl-6-ethyl-9-(phenylsulfonyl)-1,2,3,4,5,6-hexahydroazepino[4,5-b]indole (Step I, 107 mg, 0.241 mmol) in methanol (20 mL, 1 drop concentrated hydrochloric acid) is treated with palladium on carbon (10%, 32 mg) and hydrogenated at 25 psi for 48 hr. The resulting mixture is filtered, rinsing with methanol and methylene chloride, and the filtrate is concentrated to a solid. The solid is purified via chromatography (10 g SG; methanol/methylene chloride/ammonium hydroxide, 20/79/1) to give the title compound, mp=224°, dec.; IR (drift) 2982, 2935, 2743, 1473, 1449, 1312, 1300, 1151, 1091, 819, 768, 728, 691, 647 and 623 cm$^{-1}$; NMR (300 MHz, DMSO-d$_6$) 8.09, 7.85–7.95, 7.45–7.65, 4.20, 2.95–3.25 and 1.15 δ; MS (EI) m/z 354 (M$^+$), 312, 170, 167, 153, 143, 114, 78, 76 and 51; HRMS (FAB) calculated for C$_{20}$H$_{23}$N$_2$O$_2$S=355.1480, found 355.1488.

Example 9

6-Ethyl-9-[(4-fluorophenyl)sulfonyl]-1,2,3,4,5,6-hexahydroazepino[4,5-b]indole hydrochloride (IX)

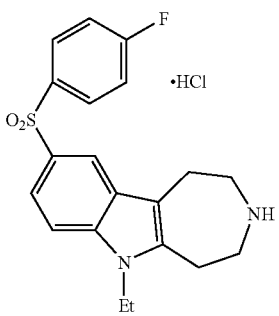

Following the general procedure of EXAMPLE 8, and making non-critical variations, 3-benzyl-9-[(4-fluorophenyl)sulfonyl]-1,2,3,4,5,6-hexahydroazepino[4,5-b]indole (EXAMPLE 2) is converted to the title compound, mp=227–233°, dec.; IR (drift) 2972, 2834, 2755, 2713, 2679, 1589, 1490, 1471, 1312, 1293, 1223, 1148, 1094, 715 and 693 cm$^{-1}$; MS (EI) m/z 372 (M$^+$), 331, 330, 171, 171, 154, 143, 143, 91 and 57; NMR (300 MHz, DMSO-d$_6$) 9.30, 8.18, 8.02, 7.55–7.70, 7.41, 4.24, 3.10–3.40 and 1.19 δ; MS (FAB) m/z 373 (MH$^+$), 372, 371, 344 and 330; HRMS (FAB) calculated for C$_{20}$H$_{22}$FN$_2$O$_2$S=373.1386, found 373.1371.

Example 10

6-Methyl-9-[(4-fluorophenyl)sulfonyl]-1,2,3,4,5,6-hexahydroazepino[4,5-b]indole hydrochloride (IX)

Following the general procedure of EXAMPLE 8, and making non-critical variations, 3-benzyl-9-[(4-fluorophenyl)sulfonyl]-1,2,3,4,5,6-hexahydroazepino[4,5-b]indole (EXAMPLE 2) is converted to the title compound, mp >300°; IR (drift) 2775, 1589, 1489, 1310, 1288, 1237, 1149, 1091, 841, 836, 805, 718, 667, 639 and 605 cm$^{-1}$; NMR (300 MHz, DMSO-d$_6$) 9.51, 8.17, 8.01, 7.63, 7.41, 3.72 and 3.10–3.45 δ.

Example 11

6-Methyl-9-[(4-trifluoromethylphenyl)sulfonyl]-1,2,3,4,5,6-hexahydroazepino[4,5-b]indole hydrochloride (IX)

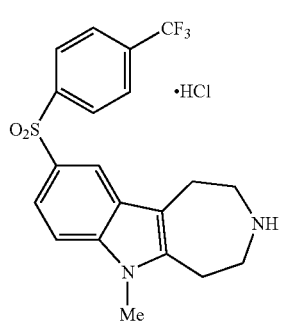

Following the general procedure of EXAMPLE 8, and making non-critical variations, 3-benzyl-9-[(4-trifluoromethyl)phenyl]sulfonyl-1,2,3,4,5,6-hexahydroazepino[4,5-b]indole (EXAMPLE 7) is converted to the title compound, mp=286°, dec.; IR (drift) 2740, 2716, 1321, 1309, 1187, 1172, 1155, 1132, 1109, 1098, 1063, 845, 719, 648 and 625 cm$^{-1}$; NMR (300 MHz, DMSO-d$_6$) 9.31, 8.19, 8.13, 7.93, 7.64, 3.71 and 3.10–3.40 δ.

Example 12

6-Ethyl-9-[(4-trifluoromethylphenyl)sulfonyl]-1,2,3,4,5,6-hexahydroazepino[4,5-b]indole hydrochloride (IX)

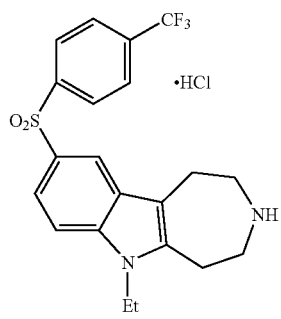

Following the general procedure of EXAMPLE 8, and making non-critical variations, 3-benzyl-9-[(4-trifluoromethyl)phenyl]sulfonyl-1,2,3,4,5,6-hexahydroazepino[4,5-b]indole (EXAMPLE 7) is converted to the title compound, mp=170–179°, dec.; IR (drift) n2762, 1326, 1302, 1294, 1190, 1184, 1171, 1153, 1138, 1109, 1095, 1064, 830, 716 and 618 cm$^{-1}$; NMR (300 MHz, DMSO-d$_6$) 9.40, 8.20, 8.14, 7.93, 7.65, 4.15–4.30, 3.10–3.45 and 1.10–1.20 δ.

Example 13

6-Methyl-9-(phenylsulfonyl)-1,2,3,4,5,6-hexahydroazepino[4,5-b]indole hydrochloride (IX)

Step I: 1-Benzoyl-4-azepanone N-[4-(Phenylsulfonyl)phenyl]hydrazone

A mixture of 1-[4-(phenylsulfonyl)phenyl]hydrazine (2.05 g, 8.26 mmol) and 4-benzoylazapanone (1.97 g, 9.09 mmol) in ethanol (40 mL) is treated with glacial acetic acid (8 drops) and heated at reflux for 1 hr. Upon cooling, the precipitate is collected, washed with ethanol and dried in the vacuum oven (50°) to give the desired hydrazone, mp=202–204°.

Step II: 3-Benzoyl-9-(phenylsulfonyl)-1,2,3,4,5,6-hexahydroazepino[4,5-b]indole

A mixture of 1-benzoyl-4-azepanone N-[4-(phenylsulfonyl)phenyl]hydrazone (Step I, 2.00 g, 4.47 mmol) in dichloroethane/phosphoric acid 84% (1/1, 40 mL) is heated at reflux for 16 hr. Upon cooling, the product is diluted with saline and extracted into methylene chloride (3×). The extracts are dried, filtered, and concentrated under reduced pressure to give a solid. The solid is purified via silica gel chromatography (Biotage 40M; ethyl acetate/heptane, 75/25) to give the desired indole.

Step III: 3-Benzoyl-6-methyl-9-(phenylsulfonyl)-1,2,3,4,5,6-hexahydroazepino[4,5-b]indole A 0° mixture of 3-benzoyl-9-(phenylsulfonyl)-1,2,3,4,5,6-hexahydroazepino[4,5-b]indole (Step II, 1.61 g, 3.74 mmol) in dry DMF (18 mL) is treated with sodium hydride (60% in oil, 165 mg, 4.11 mmol). After 30 min, the mixture is treated with iodomethane (256 μL, 4.11 mmol) and allowed to slowly warm to 20–25° under nitrogen over 16 hr. The resultant mixture is diluted with H$_2$O and filtered. The residual solid is triturated with refluxing methanol, isolated, and dried in the vacuum oven at 50° to give the desired indole, mp=254–255°.

Step IV: 6-Methyl-9-(phenylsulfonyl)-1,2,3,4,5,6-hexahydroazepino[4,5-b]indole hydrochloride A mixture of 3-benzoyl-9-(phenylsulfonyl)-1,2,3,4,5,6-hexahydroazepino[4,5-b]indole (Step III, 1.25 g, 2.81 mmol) and potassium hydroxide (1.58 g, 28.1 mmol) in ethylene glycol (30 mL) is heated at 130° under nitrogen for 92 hr. Upon cooling, the mixture is diluted with H$_2$O and extracted into ethyl acetate (3×). The combined extracts are washed with H$_2$O (2×) and saline, dried over anhydrous magnesium sulfate, filtered, and concentrated under reduced pressure to give a solid. The solid is dissolved in hot methylene chloride/methanol and treated with methanolic hydrochloric acid. The resultant mixture is concentrated and crystallized from ethyl acetate/methanol to give the title compound, mp>300°; IR (drift) 2820, 2792, 2747, 2717, 2704, 2665, 2651, 1299, 1147, 1096, 803, 729, 687, 643 and 621 cm$^{-1}$; NMR (300 MHz, DMSO-d$_6$) 9.41, 8.13, 7.85–7.95, 7.50–7.65, 3.70 and 3.10–3.40 δ; MS (EI) m/z 340 (M$^+$), 298, 157, 156, 128, 78, 74, 73, 58 and 57; HRMS (FAB) calculated for C$_{19}$H$_{21}$N$_2$O$_2$S=341.1324, found=341.1319.

Example 14

9-[(3,4-Difluorophenyl)sulfonyl]-1,2,3,4,5,6-hexahydroazepino[4,5-b]indole (IX)

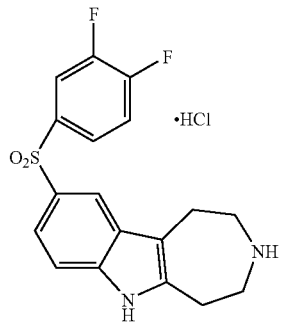

Following the general procedure of EXAMPLE 1 (steps I-III) and making non-critical variations, 1-[4-[(3,4-difluorophenyl)sulfonyl]phenyl]hydrazine (V, PREPARATION 2) is converted to the title compound, mp=320°, dec; IR (drift) 2732, 1507, 1310, 1293, 1277, 1147, 1128, 1116, 1072, 800, 751, 686, 627, 622 and 610 cm$^{-1}$; NMR (300 MHz, DMSO-d$_6$) δ 11.75, 9.50, 8.10–8.20, 7.75–7.85, 7.55–7.70, 7.40–7.50, 3.25–3.40 and 3.10–3.25; OAMS (supporting ions at): ESI+363.1, ESI-361.0.

Example 15

9-[(3,5-Difluorophenyl)sulfonyl]-1,2,3,4,5,6-hexahydroazepino[4,5-b]indole (IX)

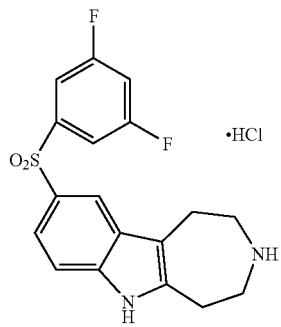

Following the general procedure of EXAMPLE 1 (steps I-III) and making non-critical variations, 1-[4-[(3,5-difluorophenyl)sulfonyl]phenyl]hydrazine (V, PREPARATION 2) is converted to the title compound, mp=313–315°, dec; IR (drift) 3256, 1606, 1591, 1307, 1285, 1269, 1153, 1138, 1122, 983, 850, 795, 678, 666 and 618 cm$^{-1}$; NMR (300 MHz, DMSO-d$_6$) δ 11.70, 9.35, 8.15–8.25, 7.40–7.85 and 3.10–3.40; MS (EI) m/z 362 (M$^+$), 333, 320, 154, 142, 127, 115, 113, 92 and 63.

Example 16

9-[(3,5-Difluorophenyl)sulfonyl]-6-methyl-1,2,3,4,5,6-hexahydroazepino[4,5-b]indole hydrochloride (IX)

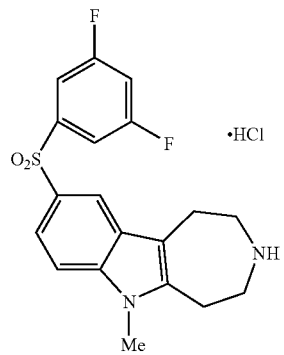

Following the general procedure of EXAMPLE 13 (steps I-IV) and making non-critical variations, 1-[4-[(3,5-difluorophenyl)sulfonyl]phenyl]hydrazine (V, PREPARATION 2) (EXAMPLE 2) is converted to the title compound, mp=337–340°, dec; IR (drift) 2767, 2750, 1603, 1437, 1308, 1295, 1144, 1129, 988, 807, 709, 681, 675, 650 and 627 cm$^{-1}$; NMR (300 MHz, DMSO-d$_6$) δ 9.35, 8.20–8.30, 7.60–7.80, 3.71 and 3.15–3.45; MS (EI) m/z 376 (M$^+$), 334, 334, 156, 114, 113, 64, 63, 57, 52 and 51; HRMS (FAB) calculated for C$_{19}$H$_{19}$F$_2$N$_2$O$_2$S=377.1135, found=377.1125.

Example 17

9-[(4-(2-Hydroxyethoxy)phenyl)sulfonyl]-6-methyl-1,2,3,4,5,6-hexahydroazepino[4,5-b]indole hydrochloride (IX)

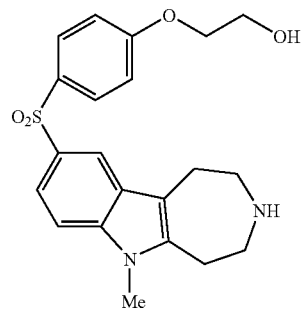

Following the general procedure of EXAMPLE 13 (steps I-IV) and making non-critical variations, 1-[4-[(4-fluorophenyl)sulfonyl]phenyl]hydrazine (V, PREPARATION 2) is converted to the title compound, mp=285–287°, dec; IR (drift) 2957, 2835, 2811, 2760, 1592, 1492, 1458, 1309, 1293, 1261, 1142, 1092, 721, 637 and 618 cm$^{-1}$; NMR (300 MHz, DMSO-d$_6$) δ 9.43, 8.09, 7.81, 7.57, 7.06, 4.85–4.95, 3.95–4.05, 3.69 and 3.00–3.45; MS (EI) m/z 400 (M$^+$), 86,

Example 18

3,6-Dimethyl-9-(phenylsulfonyl)-1,2,3,4,5,6-hexahydroazepino[4,5-b]indole (X)

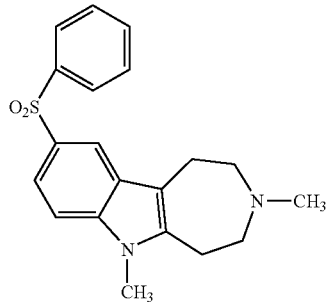

A mixture of 6-methyl-9-(phenylsulfonyl)-1,2,3,4,5,6-hexahydroazepino[4,5-b]indole (EXAMPLE 13, 341 mg, 1.00 mmol) in acetonitrile (5 mL) is treated with formaldehyde (37%, 0.400 mL, 5.00 mmol), sodium cyanoborohydride (101 mg, 1.60 mmol) and glacial acetic acid (1 drop). After 5 hr, the mixture is diluted with ethyl acetate and then washed with water and saline. The organic layer is dried, filtered, and concentrated. The concentrate is dissolved in methylene chloride/methanol and treated with methanolic hydrochloric acid. The solvent is then removed and the residual solid crystallized from hot ethyl acetate/methanol to give the title compound, mp=283–286°; IR (drift) 2523, 2477, 2453, 2428, 1479, 1311, 1304, 1283, 1150, 1094, 756, 730, 694, 644 and 623 cm$^{-1}$; NMR (300 MHz, DMSO-$d_6$) δ 11.00, 8.16, 7.85–7.95, 7.50–7.65, 3.70, 3.15–3.45 and 2.89; MS (FAB) m/z 355 (MH$^+$), 354, 353, 58 and 44; HRMS (FAB) calculated for $C_{20}H_{23}N_2O_2S$=355.1480, found=355.1488.

Example 19

3-Methyl-9-(phenylsulfonyl)-1,2,3,4,5,6-hexahydroazepino[4,5-b]indole (X)

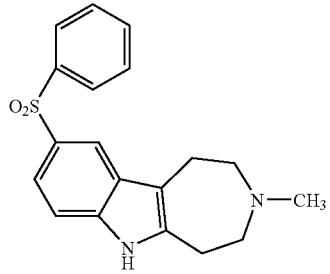

Following the general procedure of EXAMPLE 18, and making non-critical variations, 9-(phenylsulfonyl)-1,2,3,4,5,6-hexahydroazepino[4,5-b]indole (EXAMPLE 1) is converted to the title compound, mp=150°, dec; IR (drift) 2623, 1474, 1447, 1338, 1301, 1173, 1152, 1129, 1090, 755, 741, 719, 689, 673 and 615 cm$^{-1}$; NMR (300 MHz, DMSO-$d_6$) δ 11.68, 8.14, 7.85–7.95, 7.40–7.65, 3.10–3.45 and 2.88; MS (EI) m/z 340 (M$^+$), 296, 77, 74, 73, 72, 71, 58, 57, 56 and 51; HRMS (FAB) calculated for $C_{19}H_{21}N_2O_2S$=341.1324, found=341.1331.

Example 20

9-[(4-Fluorophenyl)sulfonyl]-3-isopropyl-6-methyl-1,2,3,4,5,6-hexahydroazepino[4,5-b]indole (X)

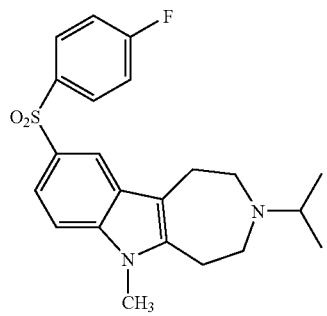

Following the general procedure of EXAMPLE 18, and making non-critical variations, 6-methyl-9-[(4-fluorophenyl)sulfonyl]-1,2,3,4,5,6-hexahydroazepino[4,5-b]indole (EXAMPLE 10)) is converted to the title compound, mp=282–283°, dec; IR (drift) 2479, 2437, 1589, 1490, 1310, 1284, 1239, 1161, 1144, 1092, 838, 809, 718, 677 and 667 cm$^{-1}$; NMR (300 MHz, DMSO-$d_6$) δ 10.60, 8.17, 7.99, 7.62, 7.39, 3.71, 3.10–3.75 and 1.31; MS (EI) m/z 400 (M$^+$), 385, 328, 315, 169, 167, 127, 85, 71, 70 and 56; HRMS (FAB) calculated for $C_{22}H_{26}FN_2O_2S$=401.1699, found=401.1709.

Examples 21–44

Following the general procedure of the above EXAMPLEs, making non-critical variations and starting with the corresponding appropriate starting materials, the following compounds are obtained:

21. 1-Methyl-9-(phenylsulfonyl)-1,2,3,4,5,6-hexahydroazepino[4,5-b]indole
22. 2-Methyl-9-(phenylsulfonyl)-1,2,3,4,5,6-hexahydroazepino[4,5-b]indole
23. 4-Methyl-9-(phenylsulfonyl)-1,2,3,4,5,6-hexahydroazepino[4,5-b]indole
24. 5-Methyl-9-(phenylsulfonyl)-1,2,3,4,5,6-hexahydroazepino[4,5-b]indole
25. 9-[(4-Fluorophenyl)sulfonyl]-1-methyl-1,2,3,4,5,6-hexahydroazepino[4,5-b]indole
26. 9-[(4-Fluorophenyl)sulfonyl]-2-methyl-1,2,3,4,5,6-hexahydroazepino[4,5-b]indole
27. 9-[(4-Fluorophenyl)sulfonyl]-4-methyl-1,2,3,4,5,6-hexahydroazepino[4,5-b]indole
28. 9-[(4-Fluorophenyl)sulfonyl]-5-methyl-1,2,3,4,5,6-hexahydroazepino[4,5-b]indole
29. 1,6-Dimethyl-9-(phenylsulfonyl)-1,2,3,4,5,6-hexahydroazepino[4,5-b]indole
30. 2,6-Dimethyl-9-(phenylsulfonyl)-1,2,3,4,5,6-hexahydroazepino[4,5-b]indole
31. 4,6-Dimethyl-9-(phenylsulfonyl)-1,2,3,4,5,6-hexahydroazepino[4,5-b]indole
32. 5,6-Dimethyl-9-(phenylsulfonyl)-1,2,3,4,5,6-hexahydroazepino[4,5-b]indole 33. 9-[(4-Fluorophenyl)sulfonyl]-1,6-dimethyl-1,2,3,4,5,6-hexahydroazepino[4,5-b]indole
34. 9-[(4-Fluorophenyl)sulfonyl]-2,6-dimethyl-1,2,3,4,5,6-hexahydroazepino[4,5-b]indole
35. 9-[(4-Fluorophenyl)sulfonyl]-4,6-dimethyl-1,2,3,4,5,6-hexahydroazepino[4,5-b]indole
36. 9-[(4-Fluorophenyl)sulfonyl]-5,6-dimethyl-1,2,3,4,5,6-hexahydroazepino[4,5-b]indole
37. 9-[(3,5-Difluorophenyl)sulfonyl]-1-methyl-1,2,3,4,5,6-hexahydroazepino[4,5-b]indole
38. 9-[(3,5-Difluorophenyl)sulfonyl]-2-methyl-1,2,3,4,5,6-hexahydroazepino[4,5-b]indole
39. 9-[(3,5-Difluorophenyl)sulfonyl]-4-methyl-1,2,3,4,5,6-hexahydroazepino[4,5-b]indole
40. 9-[(3,5-Difluorophenyl)sulfonyl]-5-methyl-1,2,3,4,5,6-hexahydroazepino[4,5-b]indole
41. 9-[(3,5-Difluorophenyl)sulfonyl]-1,6-dimethyl-1,2,3,4,5,6-hexahydroazepino[4,5-b]indole
42. 9-[(3,5-Difluorophenyl)sulfonyl]-2,6-dimethyl-1,2,3,4,5,6-hexahydroazepino[4,5-b]indole
43. 9-[(3,5-Difluorophenyl)sulfonyl]-4,6-dimethyl-1,2,3,4,5,6-hexahydroazepino[4,5-b]indole
44. 9-[(3,5-Difluorophenyl)sulfonyl]-5,6-dimethyl-1,2,3,4,5,6-hexahydroazepino[4,5-b]indole

The invention claimed is:
1. An isotopically labeled compound of formula (X)

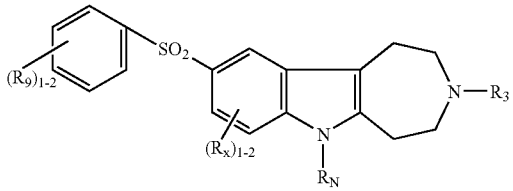

(X)

or a pharmaceutically acceptable salt or enantiomer thereof wherein $R_3$ is:
(1) —H,
(2) $C_1$–$C_4$ alkyl,
(3) $C_0$–$C_4$ alkyl-φ where -φ is optionally substituted with up to 2 of the following:
 (a) —F, —Cl, —Br, —I,
 (b) —OH,
 (c) —$OC_1$–$C_4$ alkyl,
 (d) —$CF_3$,
 (e) —C≡N,
 (f) —$NO_2$,
where $R_N$ is:
(1) —H,
(2) $C_1$–$C_4$ alkyl,
(3) $C_0$–$C_4$ alkyl-φ where -φ is optionally substituted with up to 2 of the following:
 (a) —F, —Cl, —Br, —I,
 (b) —O—$R_{N-1}$ where $R_{N-1}$ is —H, $C_1$–$C_4$ alkyl, and -φ,
 (c) —$CF_3$,
 (d) —C≡N,
 (e) —$NO_2$,
where $R_9$ is:
(1) —H,
(2) —F, —Cl,
(3) $C_1$–$C_4$ alkyl,
(4) $C_1$–$C_3$ alkoxy,
(5) —$CF_3$,
(6) $C_0$–$C_4$ alkyl-φ where -φ is optionally substituted with up to 2 of the following:
 (a) —F, —Cl, —Br, —I,
 (b) —O—$R_{9-1}$ where $R_{9-1}$ is —H, $C_1$–$C_4$ alkyl, and -φ,
 (c) —$CF_3$,
 (d) —C≡N,
 (e) —$NO_2$
(7) —$OR_{9-1}$ where $R_{9-1}$ is as defined above,
wherein the compound of formula X has an isotopic label.
2. The compound of claim 1, wherein $K_3$ is —H and $C_1$–$C_2$ alkyl.
3. The compound of claim 2, wherein $R_3$ is —H.
4. The compound of claim 1, wherein $R_N$ is —H and $C_1$–$C_4$ alkyl.
5. The compound of claim 4, wherein $R_N$ is —H, methyl, and ethyl.
6. The compound of claim 1, wherein $R_9$ is —H, —F, —Cl, $C_1$–$C_3$ alkyl, $C_1$–$C_3$ alkoxy and —$CF_3$.
7. The compound of claim 6, wherein $R_9$ is —H, —F, —Cl, C, alkyl, $C_1$ alkoxy, and —$CF_3$.
8. The compound of claim 6, wherein the $R_9$ substituent is in the 3- or 4-position.
9. The compound of claim 1, wherein the isotopic label is Carbon-11, Nitrogen-13, or Oxygen-15.
10. The compound of claim 1, wherein the compound is:
9-(phenylsulfonyl)-1,2,3,4,5,6-henhydroazepina[4,5-b]indole,
9-[(4-fluorophenyl)sulfonyl]-1,2,3,4,5,6-hexahydroazepino[4,5-b]indole,
6-ethyl-9-(phenylsulfonyl)-1,2,3,4,5,6-hexahydroazepino[4,5-b]indole, and
6-merhyl-9-(phenylsulfonyl)-1,2,3,4,5,6-hexahydroazepino[4,5-b]indole, wherein the compound has an isotopic label.
11. A compound, wherein the compound is:
3,6-dimcthyl-9-(phenylsulfonyl)-1,2,3,4,5,6-hexahydroazepin [4,5-b]indole, and
3-methyl-9-(phenylsulfonyl)-1,2,3,4,5,6-hexahydroazepino[4,5-b]indole, wherein the compound has an isotopic label.
12. A compound, wherein the compound is:
1-methyl-9-(phenylsulfonyl)-1,2,3,4,5,6-hexahydroazepino[45-b]indole,
2-methyl-9-(phenylsulfonyl)-1,2,3,4,5,6-hexahydroazepino[4,5-b]indole.
4-methyl-9-(phenylsulfonyl)-1,2,3,4,5,6-hexahydroazepino[4,5-b]indole,
5-nethyl-9-(phenylsulfonyl)-1,2,3,4,5,6-hexahydroazepino[4,5-b]indole,
1,6-dimethyl-9-(phenylsulfonyl)-1,2,3,4,5,6-hexahydroazepino[4,5-b]indole,
2,6-dimethyl-9-(phenylsulfonyl)-1,2,3,4,5,6-hexahydroazepino[4,5-b]indole,
4,6-dimethyl-9-(phenylsulfonyl)-1,2,3,4,5,6-hexahydroazepino[4,5-b]indole, and
5,6-dimethyl-9-(phenylsulfonyl)-1,2,3,4,5,6-hexahydroazepino[4,5-b]indole, wherein the compound has an isotopic (abel.
13. A method of performing diagnostic screening comprising:
incorporating an isotopically labeled compound into tissue of a mammal, wherein the isotopically labeled compound is a compound of claim 1.
14. The method of claim 13, wherein the mammal is administered a delectably labeled compound of formula X.
15. The method of claim 13, wherein the diagnostic screening is positron emission tomography.

16. The method of claim 13, wherein the diagnostic screening is single photon emission computed tomography.

17. A protected 9-arylsulfone of formula (VIII)

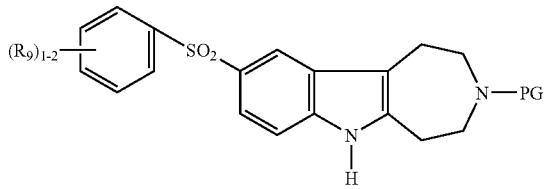

(VIII)

or a pharmaceutically acceptable salt or enantiomer thereof wherein PG is:
- (1) φ—CH$_2$—,
- (2) φ—CO—,
- (3) φ—CH$_2$—CO$_2$—, and
- (4) —CO—O—C(CH$_3$)$_3$;

where R$^9$ is:
- (1) —H,
- (2) —F, —Cl,
- (3) C$_1$–C$_4$ alkyl,
- (4) C$_1$–C$_3$ alkoxy,
- (5) —CF$_3$,
- (6) C$_0$–C$_4$ alkyl-φ where -φ is optionally substituted with up to 2 of the following:
  - (a) —F, —Cl, —Br, —I,
  - (b) —O—R$_{9-1}$ where R$_{9-1}$ is —H, C$_1$–C$_4$ alkyl, and -φ,
  - (c) —CF$_3$,
  - (d) —C≡N,
  - (e) —NO$_2$
- (7) —OR$_{9-1}$ where R$_{9-1}$ is as deined above, wherein the compound of formula VIII has an isotopic label.

* * * * *